(12) United States Patent
Rotta et al.

(10) Patent No.: US 6,894,079 B1
(45) Date of Patent: May 17, 2005

(54) METHOD FOR REDUCING FREE-RADICAL INDUCED INJURY

(76) Inventors: Alexandre T. Rotta, 63 Barker St., Buffalo, NY (US) 14209; Bradley P. Fuhrman, 83 Ashland Ave., Buffalo, NY (US) 14222; Bjorn Gunnersson, 345 Washington Hwy., Amherst, NY (US) 14226; David M. Steinhorn, 1045 Westmoor Ave., Winnetka, IL (US) 60093; Lynn J. Hernan, 83 Ashland Ave., Buffalo, NY (US) 14222

( * ) Notice: Subject to any disclaimer, the term of this patent is extended or adjusted under 35 U.S.C. 154(b) by 0 days.

(21) Appl. No.: 09/449,584

(22) Filed: Nov. 29, 1999

Related U.S. Application Data

(60) Provisional application No. 60/110,404, filed on Dec. 1, 1998.

(51) Int. Cl.[7] .................. A61K 31/025; A61K 31/02
(52) U.S. Cl. ............... 514/747; 514/759; 514/761
(58) Field of Search .................. 514/747, 761, 514/759

(56) References Cited

U.S. PATENT DOCUMENTS

| | | |
|---|---|---|
| 5,284,645 A | 2/1994 | Long, Jr. .................. 424/5 |
| 5,437,272 A | 8/1995 | Fuhrman ............... 128/203.12 |
| 5,470,885 A | 11/1995 | Fuhrman et al. ............. 514/743 |
| 5,490,498 A | 2/1996 | Faithfull et al. ....... 128/203.12 |
| 5,655,521 A | 8/1997 | Faithfull et al. ....... 128/203.12 |
| 5,733,939 A | 3/1998 | Fuhrman et al. ............ 514/759 |
| 6,054,311 A * | 4/2000 | Davey et al. ............... 435/260 |

OTHER PUBLICATIONS

Smith et al., A liquid perfluorochemical decreases the in vitro production of reactive oxygen species by alveolar macrophages, 1995, Critical Care Medicine, vol. 23 No. 9, p. 1533–1539.*

Lutz et al. "Combination of treatment with perfluorochemicals and free radical scavengers," Biomaterials, artificial cells, and immobilization biotechnology, 1992, vol. 20, pp. 951–958, Medline Abstract, AN 93004173.*

Bekyarova, G. et al., Increased Antioxidant Capacity, Suppression of Free Radical Damage and Erythrocyte Aggregability After Combined Application of Alpha–Tocopherol and FC–43 Perfluorocarbon Emulsion in Early Postburn Period in Rats; Artificial Cells, Blood Substitutes, and Immobilization Biotechnology, 1996, 24/6, pp. 629–641.

Ogilby, J.D., Cardiovascular Applications of Fluorocarbons: Current Status and Future Direction a Critical Clinical Appraisal; Artificial Cells, Blood Substitutes, and Immobilization Biotechnology, 1994, 22/4, pp. 1083–1096.

Bekyarova, G., et al., Suppressive Effect of FC–43 Perfluorocarbon Emulsion on Enhanced Oxidative Haemolysis in the Early Postburn Phase; Burns, Mar. 1997; 23(2), pp. 117–121.

Bando, K., et al., Oxygenated Perfluorocarbon, Recombinant Human Superoxide Dismutase, and Catalase Amerliorate Free Radical Induced Myocardial Injury During Heart Preservation and Transplantation; Journal of Thoracic and Cardiovascular Surgery, 1988, 96/6, pp. 930–938.

Onishchenko, N.A., et al., Use of Perfluorocarbon Emulsion in Kidney Transplantation; Khirurgiia, Jun. 1990, (6), pp. 98–103.

Lutz et al., *Combination of Treatment with Perfluorochemicals and Free Radical Scavengers*, Biomat., Art. Cells & Immob. Biotech., 1992, vol. 20(2–4), pp. 951–958.

Bekyarova et al., *Suppressive Effect of FC–43 Perfluorocarbon Emulsion on Enhanced Oxidative Haemolysis in the Early Postburn Phase*, Burns, 1997, vol. 23, No. 2, pp. 117–121.

* cited by examiner

*Primary Examiner*—Shengjun Wang
(74) *Attorney, Agent, or Firm*—Hodgson Russ LLP

(57) ABSTRACT

Disclosed are methods for reducing the injury to tissues, cells, microorganisms or lipids caused by free radicals. The method comprises exposing a composition comprising perfluorocarbon to the tissue, cell, microorganism or lipids in need of such a treatment. Perfluorocarbons may be used neat in solutions, as gases or as emulsions.

5 Claims, 8 Drawing Sheets

METHOD FOR REDUCING FREE-RADICAL INDUCED INJURY

This application claims the priority of U.S. provisional patent application, Ser. No. 60/110,404, filed on Dec. 1, 1998, the disclosure of which is incorporated herein by reference.

FIELD OF THE INVENTION

This invention relates generally to the area of free radical induced damage to tissues, cells, and cell-free lipids. More particularly, this invention provides a method for reducing free radical induced damage to tissues, cells and lipids by using compositions comprising perfluorocarbons.

BACKGROUND OF THE INVENTION

Perfluorocarbons

Perfluorocarbons (PFCs) are liquids derived from common organic compounds in which all or substantially all of the carbon-bound hydrogen atoms or other substituents have been replaced by fluorine atoms. PFCs have low surface tension and low viscosity. PFCs are clear, colorless, odorless, non-inflammable liquids that are essentially insoluble in water. PFCs are denser than water, have low surface tension and generally, low viscosity. A widely used perfluorocarbon is perfluorooctyl bromide (PFOB), also known as perflubron.

PFCs are known for their high solubility for gases. Mammals can breath certain PFCs and later resume breathing air without suffering any long-term effects. Thus, PFCs have been used for respiratory gas exchange (e.g. liquid breathing; partial liquid ventilation, Faithfull et al., U.S. Pat. Nos. 5,490,498, 5,655,521; perfluorocarbon associated gas exchange, Fuhrman et al., U.S. Pat. No. 5,437,272). Their high solubility of gases has made PFCs useful as blood substitutes (Riess, 1984, Artificial Organs, 8:34:56). Further, PFCs have also been used to reduce the inflammatory responses in tissues and have been-recently disclosed as anti-inflammatory agents (Fuhrman et al., U.S. Pat. Nos. 5,470,885 and 5,733,939).

Free Radicals

Free radicals are highly reactive structures known to cause reactions capable of damaging biomolecules in living organisms. Free radicals such as hydrogen peroxide, hydroxyl radicals, and organic free radicals are produced in vivo by enzymatic, spontaneous, radiation, and photochemical oxidation reactions, or may be generated by direct oxidative attack on cell components. Intracellular sources of free radicals include mitochondria, endoplasmic reticulum, peroxisomes, and plasma and nuclear membranes.

Free radicals can damage cell membranes by promoting peroxidation of membrane lipids, a process that has been implicated in various disease states and aging. In addition, hydroxyl radicals can cause site specific damage to DNA such as oxidation of DNA bases. Biological injury by free radicals may represent a final common pathway for inflammation in tissues. These pathways include liberation of free radicals including reactive oxygen species by cells collectively called inflammatory cells. Thus, free-radical reactions and oxidative stress appear to be basic mechanisms by which living tissues and cells are injured.

Oxidative damage to cellular mechanisms has been implicated in various conditions including photic injury to skin, carcinogenesis, aging, atherogenesis, inflammation, infection, sepsis as well as neurodegenerative, cardiovascular and respiratory diseases. Thus, there is an ongoing need to identify agents by which damage by free radicals to tissues is reduced.

SUMMARY OF THE INVENTION

Figure 1A:
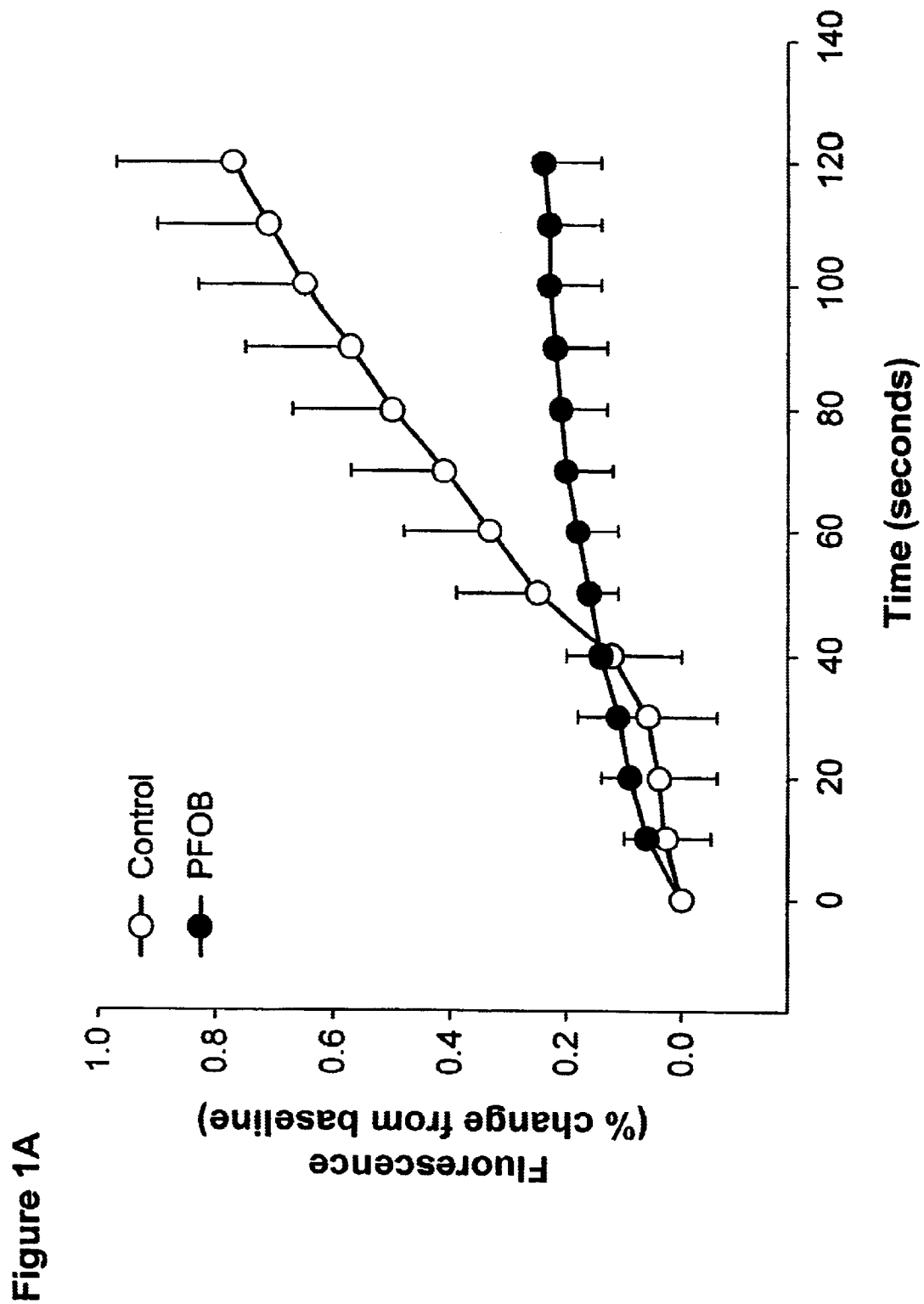
FIG. 1 is a representation of free radical generation in cells as determined by fluorescence in control cells (-●-) or cells protected with perfluorocarbon (-○-).

The present invention provides a method for reducing free-radical induced damage to tissues, cells, and cell-free lipids. The method comprises the steps of exposing the tissue, cell, or cell-free lipids to a pharmacologically effective amount of perfluorocarbons. The present invention also provides formulations comprising PFCs for free-radical-effect reducing applications.

In one embodiment of the invention, PFC compositions are provided for skin applications so as to reduce the effect of free radical damage that occurs in conditions such as, but not limited to photic, radiation and chemical stimulation.

In another embodiment of the invention a method is provided for reducing free radical damage to tissues including but not limited to epidermis, pulmonary tissue, gastrointestinal tissue and systemic tissue.

In another embodiment, a method is provided for reducing free radical damage to cells or microoganisms in culture.

In another embodiment, a method is provided for reducing free radical damage to lipids in non-cellular systems.

DETAILED DESCRIPTION OF THE INVENTION

The present invention provides a method for reducing or preventing free-radical induced injury to tissues. The method involves contacting the tissue with a perfluorocarbon comprising composition. The method of the present invention is useful for reducing or preventing free-radical damage due to non-inflammatory conditions. Non-inflammatory conditions include, but are not limited to, photic injury (e.g. sunburn), radiation injury, toxic injury, direct oxidative injury (e.g. oxygen toxicity), and aspect of atherogenesis, carcinogenesis, neurodegeneration, certain toxin injuries, and direct oxygen toxicity to lung and brain as in neural syndrome and deep sea diving.

Other uses include prevention of free radical attack on cells or microorganisms in culture and protection of lipids in non-cellular systems.

Perfluorocarbons of the present invention include straight or branched chain, or cyclic structures (Riess, supra). These molecules may have some degree of unsaturation, and may also contain bromine or hydrogenations, or they may be amine derivatives. The perfluorocarbons suitable for the present invention are similar to those useful in respiratory gas exchange methods. Suitable perfluorocarbons include FC-75, FC-77, RM-101, Hostinert 130, APF-145, APF-140, APF-125, perfluorodecalin, perfluorooctylbromide, perfluorobutyltetrahydrofuran, perfluoropropyltetrahydropyran, dimethyladamantane, trimethylbicyclononane, and combinations thereof. In a preferred embodiment, the perfluorocarbon is perflubron (PFOB)

In one embodiment of the invention, a method is provided for the use of PFCs in reducing or preventing injury to tissues or cells caused by free radicals. For the method of the present invention, perfluorocarbons can be used as neat liquids, gases, or emulsions in pharmacologically effective amounts. A pharmacologically effective amount refers to an amount effective in reducing the deleterious effect of free radicals on normal cells. It will be appreciated by those skilled in the art that the pharmacological effective concentration of the perfluorocarbon based composition in the formulation will depend on other ingredients in the formulation, the mode of administration of the formulation, and the physiologic site to be treated.

PFCs can be used in formulations suitable for the specific tissue in need of such treatment. For example, for using PFCs neat, the compounds can be placed into sterile, isotonic formulations and may contain additional components like conventional stabilizers and incipients. Emulsions of PFCs may be prepared by methods well known in the art. Such emulsions are typically fluorocarbon-in-water emulsions having a fluorocarbon phase and an aqueous phase. U.S. Pat. No. 5,470,885 to Fuhrman et al. discloses such emulsions, which method is hereby incorporated by reference. For use in a gaseous form, perfluorocarbon saturated vapor or PFC droplets in the form of a mist or air-borne suspension delivered using a nebulizer or atomizer can be used.

In another embodiment, a method is provided for reducing free-radical induced damage to cells or microorganisms in culture. For this embodiment, PFCs can be used as neat liquids, as emulsions or as a component of nutrient mixtures.

In another embodiment, a method is provided for reducing free-radical induced damage to cell-free lipids. For this embodiment, PFCs can be used as neat liquids, as emulsions, or dissolved in the lipid to be protected.

In another embodiment, formulations are provided for administration to various tissues. For topical application, PFCs can be used in lotions, creams, gels, suppositories and the like. Suitable bases for topical applications are known to those skilled in the art and include lanolin, propylene glycol, mineral oil, vegetable or flower oils, glycerin, glyceryl stearate, cetyl alcohol, propylparaben and the like. The composition may also include: preservatives, fragrances and the like. For treatment of free-radical damage to pulmonary tissues, for example in oxygen toxicity to lungs, PFCs may be administered intratracheally in a gaseous form. For free radical injury to gastrointestinal tract, PFCs may be administered orally or rectally. For systemic application, PFCs may be administered intravenously, intramuscularly, or by other means known to those skilled in the art.

In another embodiment, the PFC composition may be incorporated into a tablet (including capsule, caplet, and the like). Suitable bases are known to those skilled in the art to include fillers, binders, coatings, excipients and combinations thereof. For example, base ingredients include plant cellulose, natural silica, magnesium stearate, was, vegetable glycerides, vegetable stearate, and a combination thereof.

Effects on free radical attack appear to require little contact with perfluorocarbon. Low concentrations and small quantities may be effective if they provide to the target of attack a quantity of perfluorocarbon that it may dissolve, store or concentrate. Thus, for certain applications, neat (100%) perfluorocarbon may be required, but for other, small quantities or low concentrations may suffice.

The compositions of the present invention may be administered prior to, simultaneously or following exposure to free radical inducing agents including, but not limited to, toxins, radiation and heat. Exposure to free-radical inducing agents may be incidental, or accidental, or predetermined.

Other objects, features, and advantages of the present invention will become apparent from the following drawings and examples which are to be construed as illustrative and not restrictive.

EXAMPLE 1

Perfluorocarbon Protects Cell Monolavers Against Direct in Vitro Oxidative Injury This embodiment of the invention demonstrates the effectiveness of PFCs against free radical injury to cells in vitro. An endothelial cell culture system was utilized to demonstrate a protective effect of PFCs. Rat pulmonary artery endothelial cells (RPAECs) were grown to confluence on optical grade culture dishes using standard technique. Cells were grown in Dulbecco's Modified Eagles Medium (high glucose) containing 1 M HEPES, 0.8 M NaOH 10% serum (calf serum). Cells were incubated at 37° C. in 5% $CO_2$, 95% relative humidity.

An oxidative stress indicator, dichlorofluorescein diacetate (DCFDA), was used to indicate the extent of injury to cells. DCFDA is a colorless substance that permeates through the cell membrane. Fresh DCFDA (5 uM) was prepared by solubilizing 2.4 mg DCFDA in 300 ul DMSO, then diluting the solution in 1000 ml Phosphate buffered saline (PBS), pH 7.4. Immediately prior to the experiment, the culture medium was removed and the buffer containing DCFDA was added to the culture dish. Cells were incubated for 15 minutes to allow for the DCFDA probe to enter the cells. Upon excitation by contact with free radicals, the dye DCFDA becomes fluorescent and the intensity of fluorescence is directly proportional to the degree of oxidative stress suffered by the cells. After the incubation period, the DCFDA containing buffer was removed and the cells were washed with PBS (three times) to remove any residual DCFDA from the extracellular space.

To generate free radicals, a buffer containing 10 mM $H_2O_2$ in PBS was used to promote oxidative stress to cell monolayers. Culture dishes were exposed to perflubron which was then either removed by evaporation or by aspiration. Thus, in one set of culture dishes (FIG. 1A), cell monolayers were exposed to perflubron (PFOB) by adding 1 ml of perfluorocarbon to the culture dish. Cell monolayers not exposed to PFOB served as controls. After an incubation period of 1 minute, PFOB was aspirated from the culture dish using a fine glass pipette and cell monolayers were washed with PBS.

In another set of culture dishes (FIG. 1B), cell monolayers were exposed to perfluorocarbon by adding 1.0 ml of perflubron to the culture dish. Cells monolayers not exposed to PFOB served as controls. After an incubation period of 1 minute, PFOB was removed from the culture dish using a glass pipette and any residual perflubron was allowed to evaporate prior to washing the cell monolayers with PBS.

Oxidative stress was initiated by the addition of the buffer containing 10 mM $H_2O_2$ in PBS to the cell monolayers.

Oxidative stress to cells was measured by sequential imaging with a confocal laser microscope obtained at baseline and every 10 seconds for 120 seconds. The excitation filter was wet at 488 nm and the images were read at 515 nm. The images were stored as digital files and were subsequently subjected to histogram analysis by dedicated software to quantify objective differences in oxidative injury to cells per high power field.

Figure 1B:
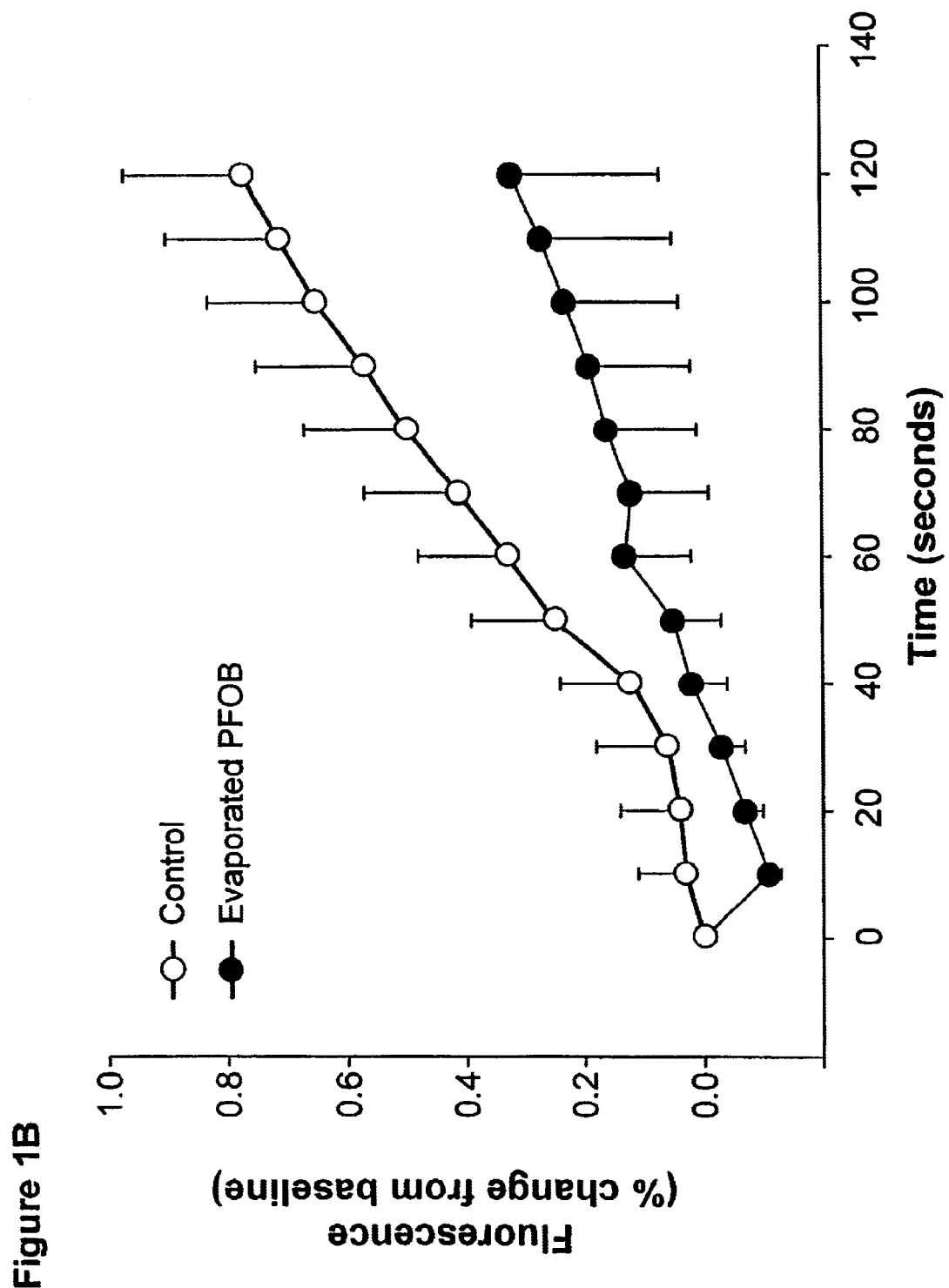
Figure 2:
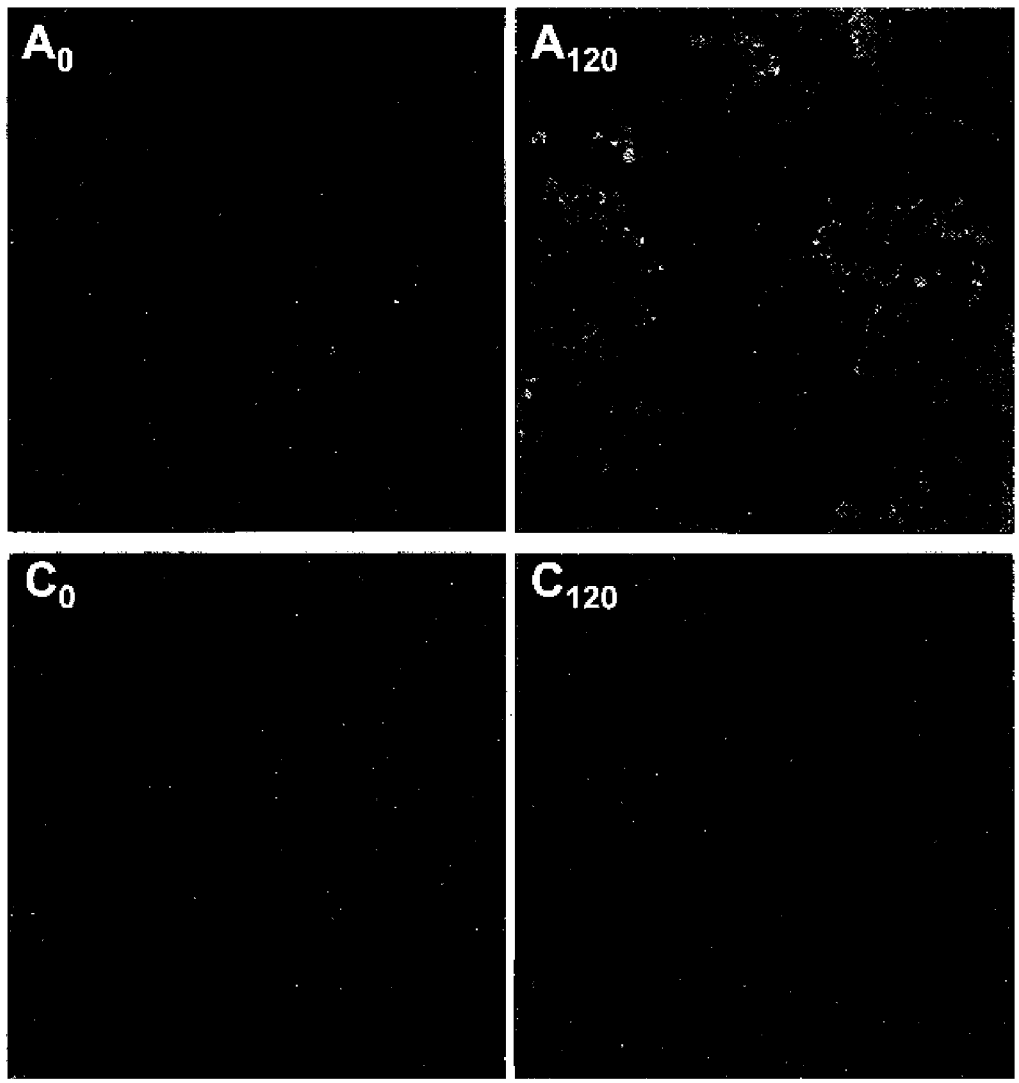
FIG. 2 is a photomicrograph of cells wherein the fluorescence is an indicator of free radicals in cells protected with (lower panel) or without (upper panel) perfluorocarbon.
Figure 3:
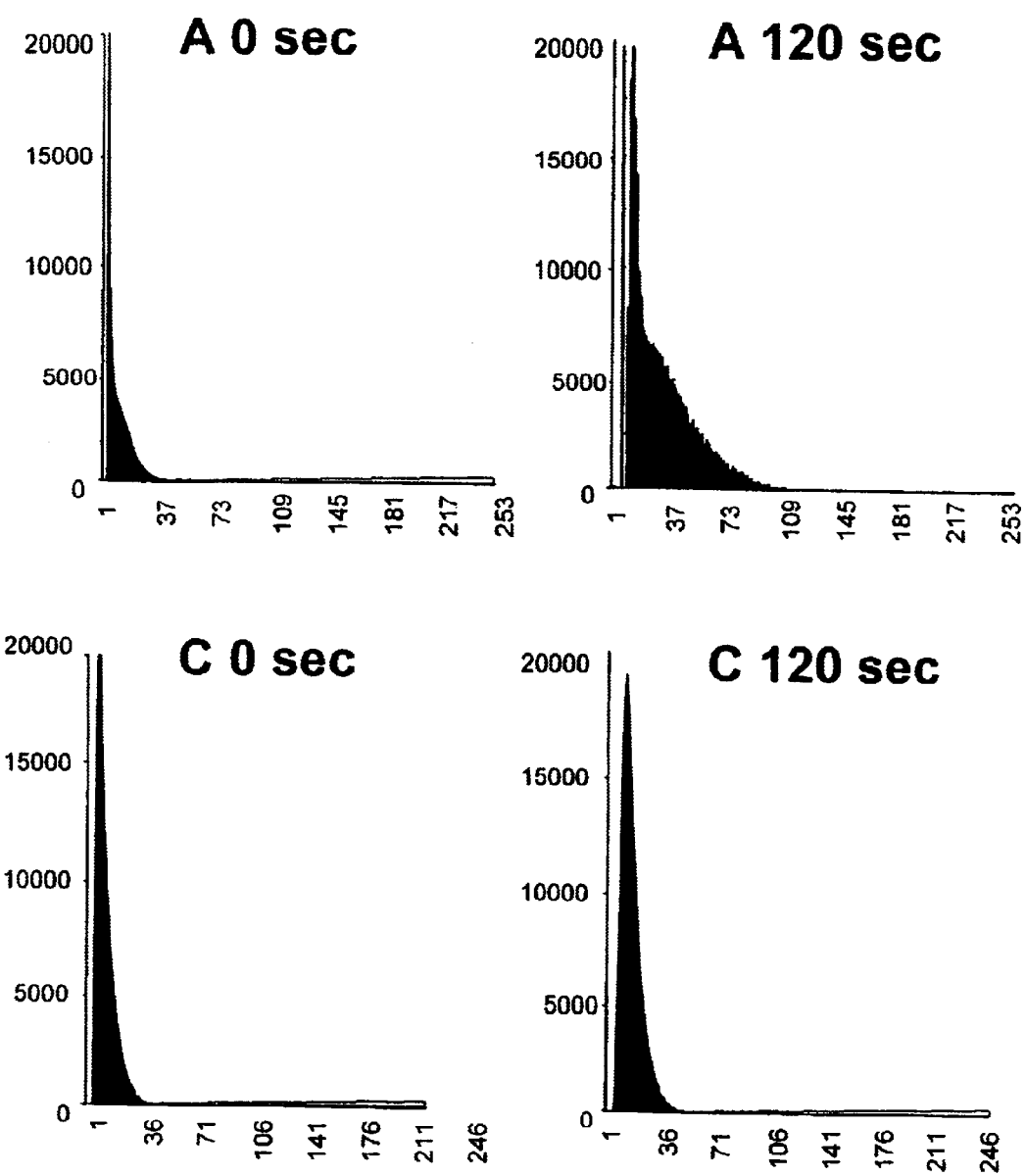
FIG. 3 is a quantitative representation of the fluorescence of cells from FIG. 2.

Relative fluorescence of cell monolayers exposed to perflubron (open circles) and standard buffer (closed circles) are shown in FIG. 1. The upper panel (FIG. 1A) depicts the experiment where perflubron was removed from the culture dishes by aspiration before application of the oxidative stress. The lower panel (FIG. 1B) depicts the experiment where perflubron was removed by aspiration and allowed to evaporate. Data are expressed as mean+standard error of the mean. Digital images of representative cell monolayers from FIG. 1 are shown in FIG. 2. $A_0$ and $C_0$ represent the baseline fluorescence before exposure to oxidative stress. $A_{120}$ and $C_{120}$ represent fluorescence after 120 seconds of oxidative stress in cultures exposed to perfluorocarbons ($C_{120}$) or control cultures ($A_{120}$). Quantitative analysis of the fluorescence in cell cultures from FIG. 2 is shown in FIG. 3. A lack of fluorescence, indicating the absence free-radicals, is observed in cultures protected with PFOB ($C_{120}$). Thus, as shown in FIGS. 1, 2 and 3, perfluorocarbon attenuates oxidative injury to cell monolayers.

EXAMPLE 2

Perfluorocarbon Protects Against Fatty Acid Oxidation

This embodiment illustrates the effect of perfluorocarbon on fatty acid oxidation in a non-biological system (fatty acid micelles). Linoleic acid micelles were prepared as follows: Linoleic acid (3 mM) was emulsified into phosphate buffered saline (PBS) using the detergent sodium dodecyl sulfate (SDS, 250 $\mu$M). Linoleic acid/SDS micelles in PBS were formed by agitation and sonication of the resulting emulsion. The emulsion (5 ml) was exposed to perfluorocarbon by the addition of perflubron (PFOB, 5 ml, available commercially) to the system. Emulsions not exposed to perflubron served as controls. The emulsion/PFOB system (PFOB exposed micelles) and the non-exposed micelles (control) were agitated (xyz axial shaker) at room temperature. Oxidative stress was applied to the system by the addition of various concentrations (2–50 mM) of AAPH, an azo-compound that generates peroxyl radicals at a constant rate while undergoing spontaneous thermal decomposition. The degree of oxidative injury to the linoleic acid/SDS micelles was assessed by measuring malondialdehyde concentrations in aliquots taken from the emulsion phase at different time intervals. Malondialdehyde, a product of lipid peroxidation, is a reliable indicator of oxidative stress to lipid compounds. Malondialdehyde was measured using the method of Esterbauer and Cheeseman (*Meth. Enzymol.* 1990; 186:407–421). Briefly, 200 $\mu$l aliquots of the emulsion taken at different time points in a sequential fashion were mixed with a solution containing one volume of methanol and three volumes of 10.3 mM -methyl-2-phenylindole in acetonitrile (6.50 $\mu$l). After agitation, 37% hydrochloric acid (150 $\mu$l) was added to the solution, agitated and incubated for 60 minutes at 450 C. Absorbance changes were measured using a spectrophotometer (Beckman DU 650, Beckman Instruments) at 586 nm, against standard curves of 1,1,3,3-tetramethoxypropane at the end of the incubation period.

Figure 4A:
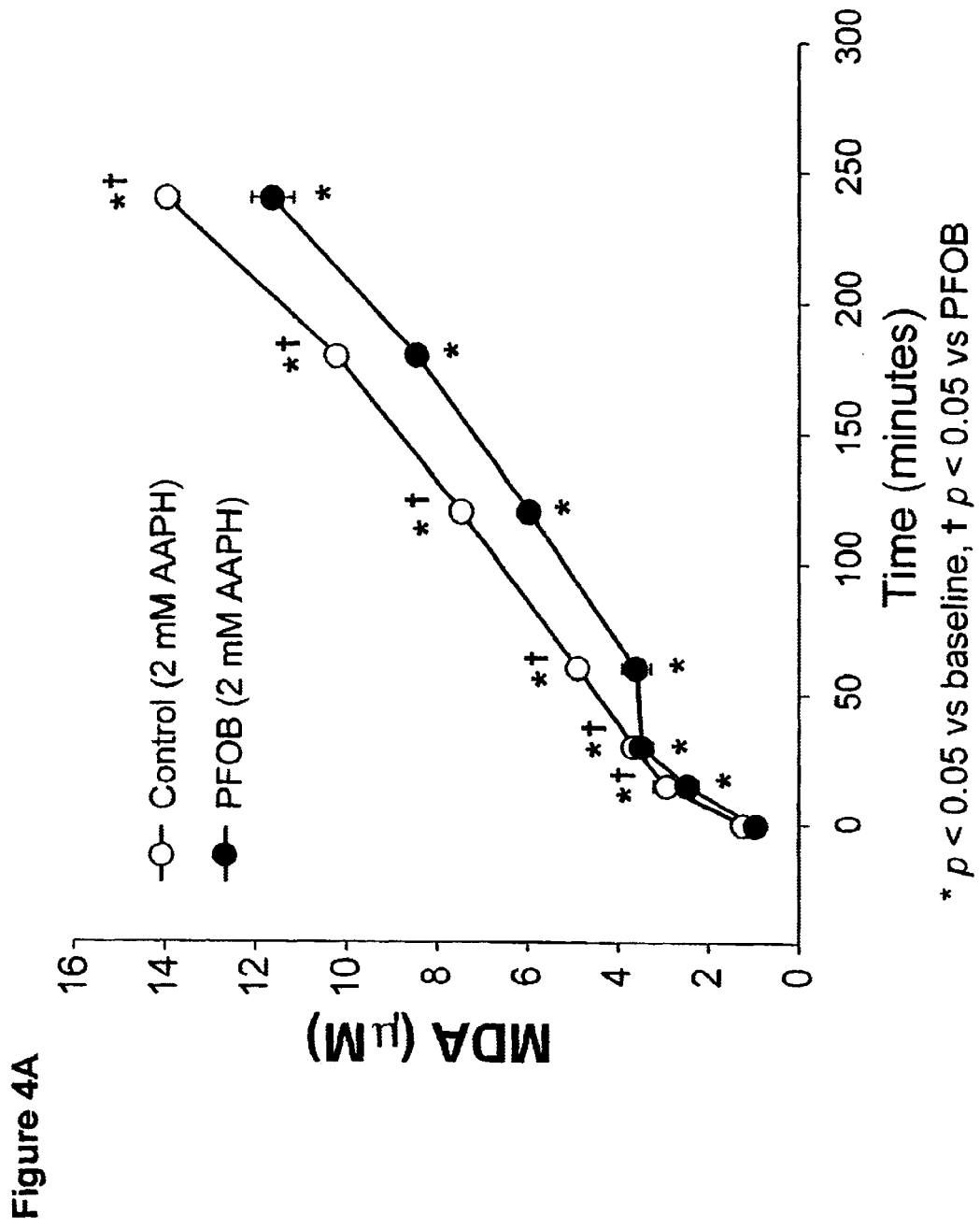
FIGS. 4A–D is a representation of malondialdehyde formation in the presence of a peroxyl radical donor for perfluorocarbon-treated and control fatty acid micelles
Figure 4B:
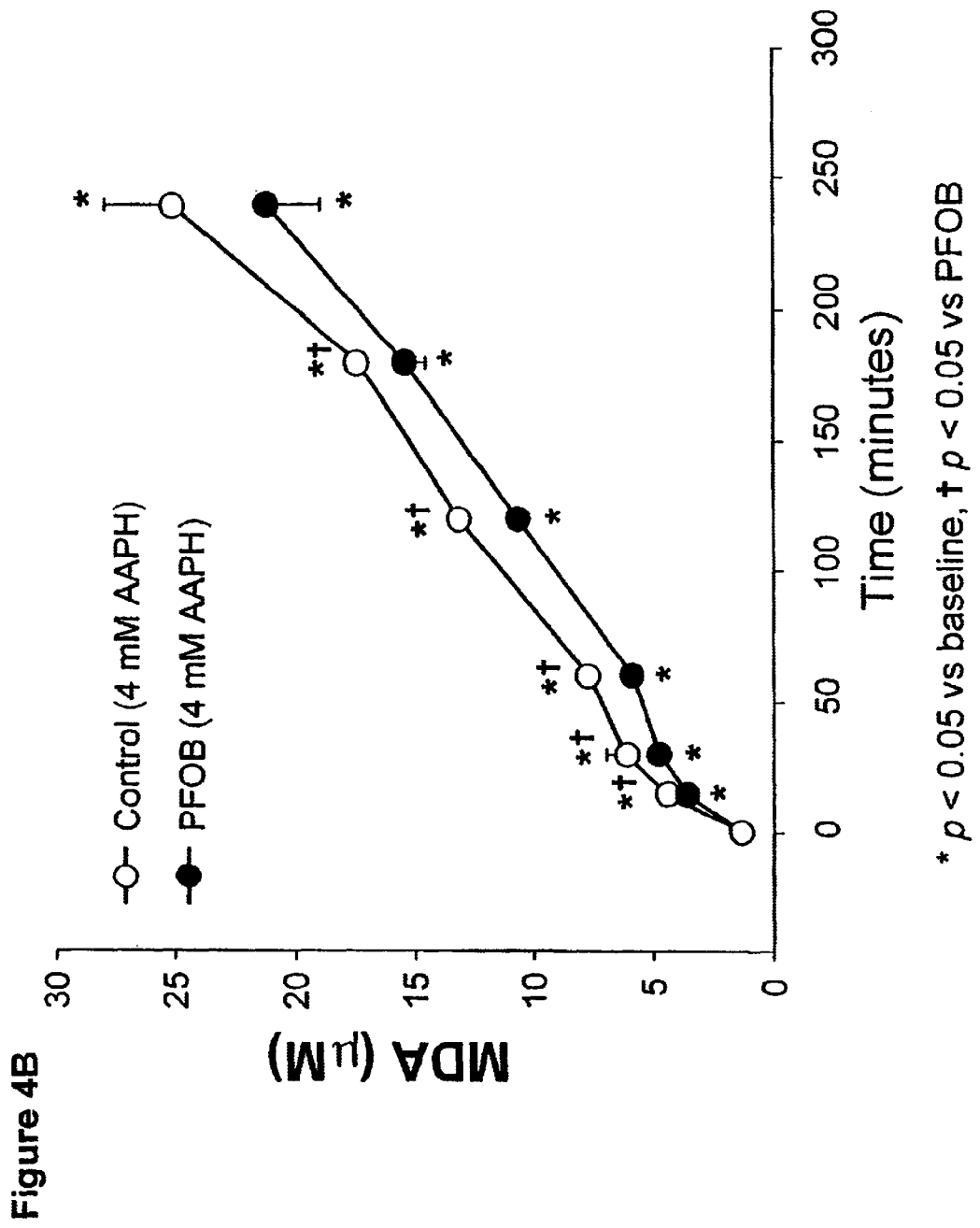
Figure 4C:
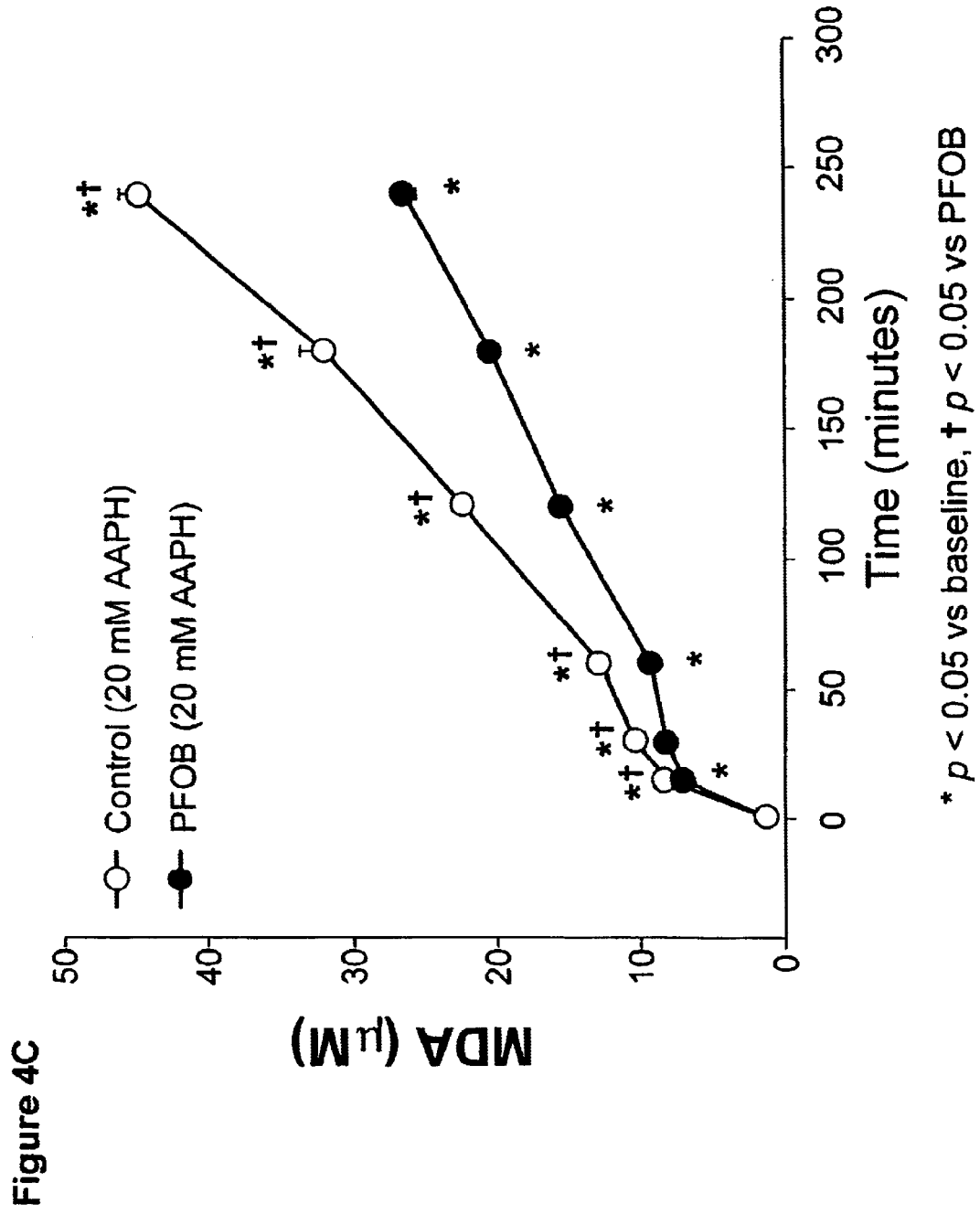
Figure 4D:
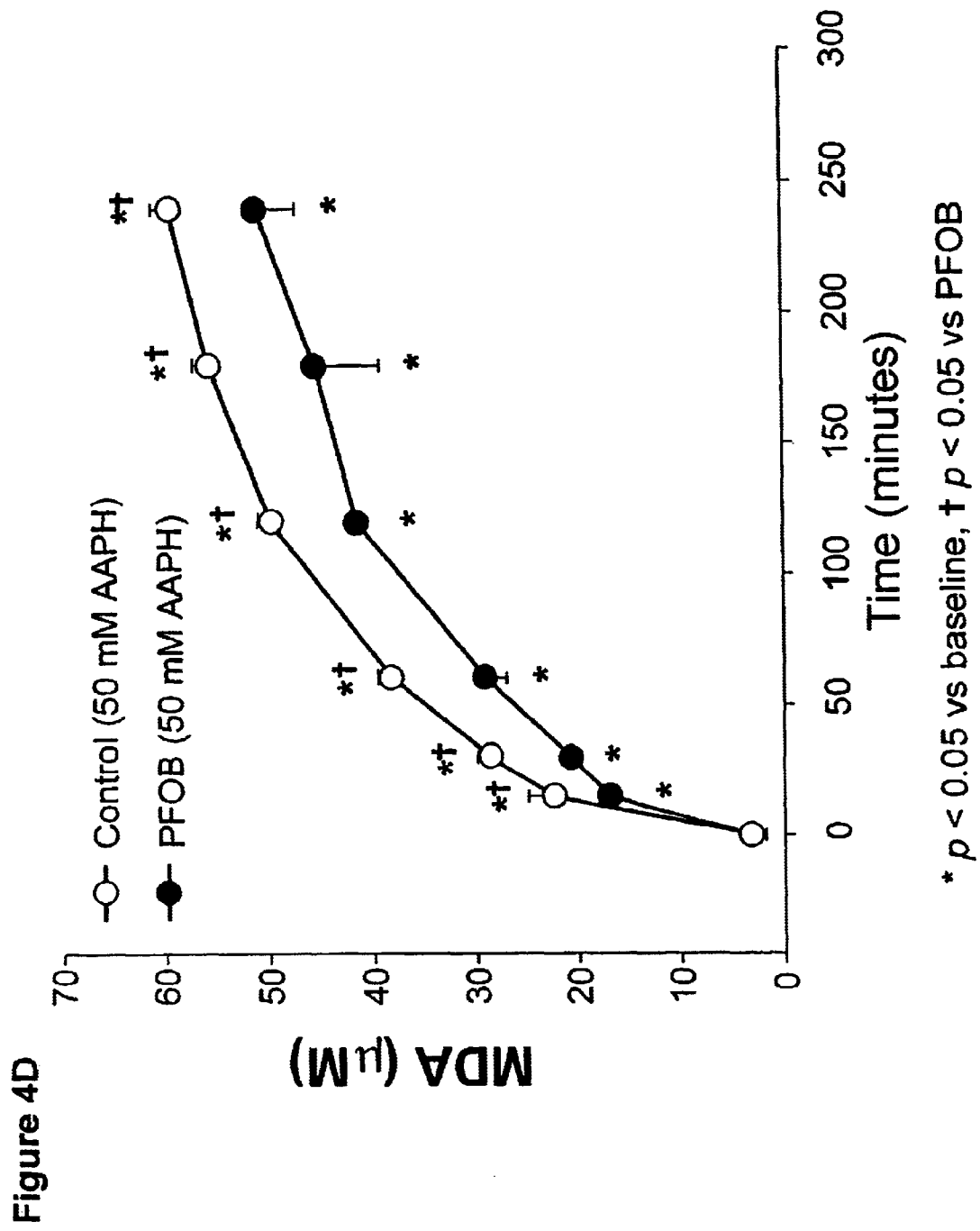

FIGS. 4A–D indicate the MDA concentrations in the presence (open circles) or absence (closed circles) of perflubron at 2 mM AAPH (FIG. 4A), 4 mM AAPH (FIG. 4B), 20 mM AAPH (FIG. 4C), and 50 mM AAPH (FIG. 4D). Data are mean+Standard deviation. *$p<0.005$ vs. baseline. †$p<0.05$ vs. PFOB.

This experiment demonstrates that perfluorocarbon attenuates oxidative damage to fatty acid micelles. Although not intending to be bound by any particular theory, this effect may account for the decreased oxidative damage to injury-prone tissues exposed to perfluorocarbons in vivo.

From the foregoing, it will be obvious to those skilled in the art that various modifications in the above-described methods, and compositions can be made without departing from the spirit and scope of the invention. Accordingly, the invention may be embodied in other specific forms without departing from the spirit of essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A method for reducing free-radical induced injury in vitro to cells in need of protection from exogenons free radicals wherein the cells are exposed to exogenous fee radicals in an amount sufficient to cause injury to the cells, comprising the step of contacting the cells with a therapeutically or prophylactically effective amount of perfluorocarbon before, during or after exposure of the cells to erogenous free radicals, wherein the free-radical induced injury to the cells is reduced in the presence of the perfluorocarbon.

2. The method of claim 1, wherein the free-radical injury is caused by a stimulus selected from the group consisting of photic, radiation and chemical.

3. The method of claim 2, wherein the chemical stimulus is an oxidative stimulus.

4. The method of claim 1, wherein the perfluorocarbon is perflubron.

5. The method or claim 1, wherein the cell is a microorganism.

* * * * *

UNITED STATES PATENT AND TRADEMARK OFFICE
CERTIFICATE OF CORRECTION

PATENT NO. : 6,894,079 B1
DATED : May 17, 2005
INVENTOR(S) : Rotta et al.

It is certified that error appears in the above-identified patent and that said Letters Patent is hereby corrected as shown below:

Title page,
Item [76], Inventors, "Gunnersson" should be -- Gunnarsson --.

Column 6,
Line 36, "exogenons" should be -- exogenous --.
Line 37, "fee" should be -- free --.
Line 41, "erogenous" should be -- exogenous --.

Signed and Sealed this

Sixth Day of September, 2005

JON W. DUDAS
*Director of the United States Patent and Trademark Office*